United States Patent [19]

Hargest, III

[11] 4,249,535

[45] Feb. 10, 1981

[54] GASTRIC FEEDING DEVICE

[76] Inventor: Thomas S. Hargest, III, 1078 Winslow Dr., Charleston, S.C. 29412

[21] Appl. No.: 8,554

[22] Filed: Feb. 2, 1979

[51] Int. Cl.[3] ........................ A61M 25/00; A61J 15/00

[52] U.S. Cl. .................................... 128/348; 128/222

[58] Field of Search ............... 128/222, 240, 246, 276, 128/348–351

[56] References Cited

U.S. PATENT DOCUMENTS

| | | | |
|---|---|---|---|
| 1,596,754 | 8/1926 | Moschelle | 128/350 R |
| 2,508,690 | 5/1950 | Schmerl | 128/276 |
| 2,603,217 | 7/1952 | McShirley | 128/239 |
| 2,614,563 | 10/1952 | Devine | 128/276 |
| 3,058,472 | 10/1962 | Thornton | 128/348 |
| 3,500,819 | 3/1970 | Silverman | 128/348 X |
| 4,134,405 | 1/1979 | Smit | 128/348 X |
| 4,182,342 | 1/1980 | Smith | 128/348 |

FOREIGN PATENT DOCUMENTS

| | | | |
|---|---|---|---|
| 2380034 | 10/1978 | France | 128/348 |

*Primary Examiner*—Dalton L. Truluck

*Attorney, Agent, or Firm*—Wellington M. Manning, Jr.; Luke J. Wilburn, Jr.

[57] ABSTRACT

A gastric feeding device for introduction into the stomach of a patient from the nasal or oral opening thereof comprising an elongate flexible collapsible tube having a longitudinal passageway with a wall thickness incapable of independently sustaining a tubular shape in the absence of internal support in the longitudinal passageway, a relatively rigid fitting having a through passageway attached to the proximal end of the collapsible tube for introducing an elongate flexible support tube into the length of the passageway to support the same during intubation, and for introducing a fluid into and throughout the length of the collapsible tube passageway to contact the inner wall surface thereof after intubation to permit removal of the support tube therefrom. The support tube engages the closed distal end of the collapsible tube to maintain the relative positions of the support tube and collapsible tube, and/or a water-soluble adhesive material may be applied to the outer surface of the support tube and inner surface of the collapsible tube to secure the relative positions thereof during intubation.

9 Claims, 4 Drawing Figures

GASTRIC FEEDING DEVICE

This invention relates to a gastric feeding device for a medical patient, and, more particularly, to an elongate tubular device for insertion into the stomach area of a patient who is unable to eat normally in order to introduce nutrients and other fluids.

In order to feed premature infants, post-operative patients, seriously ill patients, or any other patients incapable of normal eating, a gastric feeding tube is usually passed through the nose and esophagus of the patient into the stomach. Since a patient must be fed several times each day, the tube is most generally left in place and the outer end thereof sealed off when not in use. During intubation of a patient, it can be understood that the tubular object is pushed from a position outside the nose area to locate the distal end of the tube in the patients's stomach.

Since the tubes of the prior art must have sufficient longitudinal rigidity to be passed downwardly into the stomach during intubation, they are generally of a relatively hard nature to permit intubation and to maintain an orifice for the passage of fluids out of the tube. Because of the hard nature of the tubes, they tend to be quite uncomfortable, as well as to irritate tissues of the nasal and esophageal passageways of the patient when they are left in the stomach for an extended period of time. However, such irritations have heretofore been accepted because of the less desirable and more discomforting practice of introducing and removing the tube before and after each feeding.

It is therefore an object of the present invention to provide an improved gastric feeding device which may be introduced through the nose of a patient into the patient's stomach, and which device may be left in place for considerable periods of time with minimum irritation and less discomfort to the patient than has been experienced with aforementioned devices of the prior art.

It is another object of the present invention to provide a gastric feeding device for a medical patient which may be employed to introduce fluids into the stomach, or, in cooperation with an additional tubular element, to remove fluids from the stomach of the patient when desired.

Broadly, the present invention comprises an elongate, flexible, collapsible tube having a longitudinal passageway therethrough and a wall of sufficient thinness to be incapable of independently sustaining a tubular shape in the absence of internal support in the longitudinal passageway of the tube, such that the tube, when not in use but when in place in the patient, will collapse laterally of its longitudinal axis to provide minimum restriction and irritation of tissues of the body passageways through which it extends. The proximal end of the tube is provided with a short tubular fitting of relatively rigid construction which has openings therein for receiving an elongate, flexible support tube throughout the length of the collapsible tube to permit intubation of the patient, and for introducing a fluid throughout the length of the collapsible tube passageway to permit ready removal of the support tube from the collapsible tube after intubation. The distal end of the collapsible tube contains suitable wall surfaces, or may be provided with a water soluble adhesive, to engage the support tube and maintain its position in the collapsible tube during intubation, while permitting ready removal of the support tube upon completion of intubation.

The invention will be better understood, and the above as well as other objects of the invention will become more apparent, from the following detailed description of several embodiments of the invention, when taken together with the accompanying drawings, in which.

Figure 1:
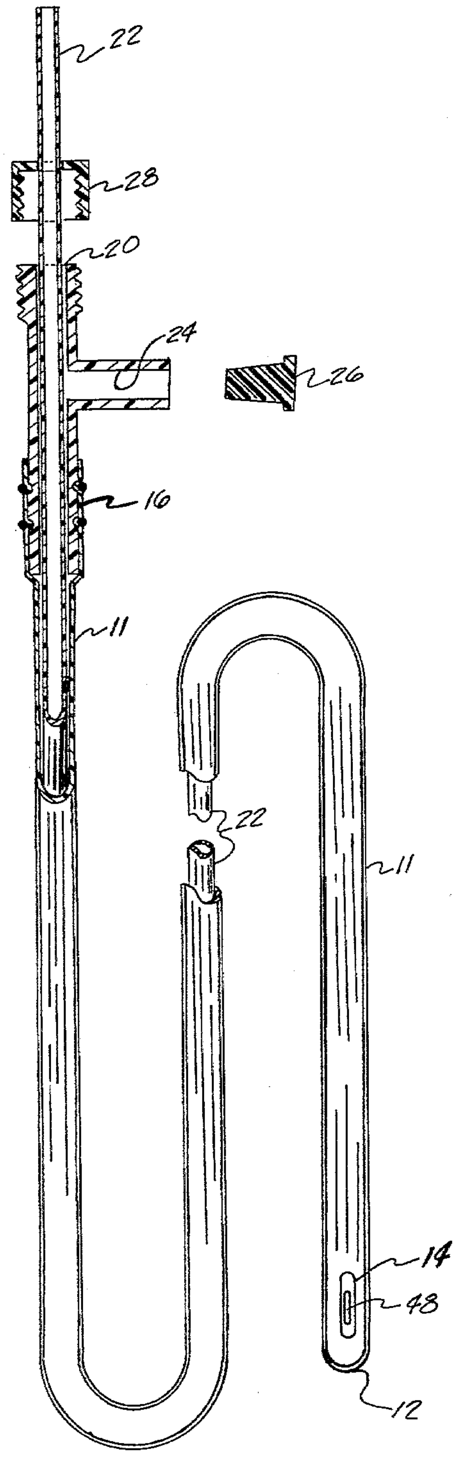
FIG. 1 is a side elevation view of the feeding device of the present invention, with the upper portion of the feeding device and an internal support tube employed therewith shown in section.

Referring more particularly to FIG. 1, the gastric feeding device of the present invention comprises an elongate, flexible collapsible tube 11 having a longitudinal passageway and a peripheral wall of sufficient thinness that the collapsible tube 11 is incapable of independently sustaining a tubular shape in the absence of internal support in the passageway of the tube, that is, the tube will normally collapse laterally of its longitudinal axis in the absence of any internal supporting medium. To accomplish these ends, the tube may be formed of suitable material, such as latex, thin flexible plastic, or other like material having a wall thickness such that the tube will normally collapse laterally upon itself. In the embodiment shown in FIGS. 1 and 2, the distal end 12 of the tube is closed, and one or more lateral openings 14 are provided in the wall of the tube adjacent the closed end to provide for discharge of fluid material therefrom.

The proximal end portion 16 of collapsible tube 11 is provided with a short, tubular fitting 18 formed of a relatively rigid material, self-sustaining in shape, and having a top opening 20 for introduction of a flexible but relatively hard support tube 22 into and throughout the length of the collapsible tube passageway. Support tube 22 may be formed of a suitable flexible plastic material, self-sustaining in shape, and generally may be of the type heretofore employed for patient intubation in the prior art. Extending from the fitting 18 intermediate its length is a side tube passageway 24 having an opening with closure plug 26 for introduction of fluid and fluent materials to be passed into the stomach of the patient. The upper opening 20 of the rigid tube is also provided with suitable closure cap means 28 with central opening whereby the opening 20 may be sealed when the support tube 22 is received therein.

Figure 2:
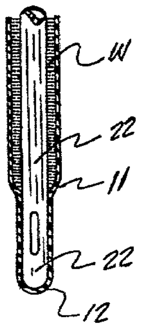
FIG. 2 is a sectional elevation view of the distal end portion of the device of FIG. 1.

Prior to intubation of the patient, internal support tube 22 is passed into the length of the collapsible tube to abut the wall of the distal end of the tube, as seen in FIG. 2. If the lateral opening 14 of tube 11 is a sufficient distance above the closed end of the tube, the abutment of the support tube 22 with the closed end of collapsible tube 11 may be sufficient to maintain the position of the support tube thereat during intubation. However, when desired or if deemed necessary, additional fastening means, such as a water-soluble adhesive 32 (FIG. 4), may be employed between the wall surfaces of the collapsible tube and support tube to ensure their relative position during intubation. The adhesive may be of any suitable type compatible with the tube material and non-toxic to the human body.

Figure 4:
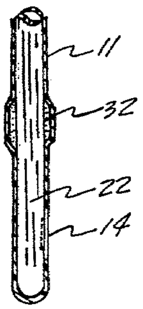
FIG. 4 is a sectional elevation view of another modified form of distal end portion of the feeding device of FIG. 1.

After intubation and proper location of the distal end of collapsible tube 11 in the patient's stomach, it can be appreciated that support tube 22 must be withdrawn from the tube 11 without disturbing the position of the distal end 12 of the tube in the stomach. This is accomplished by passing a small amount of liquid, such as water, through the side opening and passageway 24 of fitting 18 to flow between the outer wall surface of support tube 22 and the inner wall surface of the collapsible tube 11 (as illustrated at W in FIGS. 2), thereby separating the two tubes while lubricating their surfaces to permit ready removal of the support tube. If a water-soluble adhesive is employed at the distal end of the tubes, as illustrated in FIG. 4, the lubricating water employed for removing the support tube will dissolve the adhesive, after which the support tube is easily removed, as indicated above.

Figure 3:
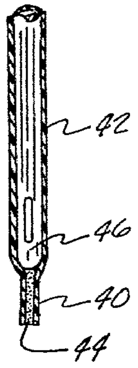
FIG. 3 is a sectional elevation view of a modified form of distal end portion of the feeding device of FIG. 1.

FIG. 3 illustrates a modified form of collapsible support tube of the present invention wherein the distal end 40 of the collapsible tube 42 is initially formed open, but the opening is temporarily sealed closed by use of a water-soluble adhesive 44. During intubation, the support tube 46 abuts the sealed end of the collapsible tube to maintain the proper relative positions of the two tubes. After proper intubation, the support tube 46 is withdrawn in the same manner as described above, with water supplied between the walls of the two tubes to lubricate the same and dissolve the adhesive 44 to open the distal end of the collapsible tube for introducing material into the patient's stomach.

After removal of the support tube, opening 20 or 24 in fitting 18 may be closed with a suitable plug and liquid materials may be directed into the stomach of a patient through the other fitting opening and collapsible tube into the stomach. Upon completion of feeding, the collapsible tube is left in place in the patient's body and collapses laterally upon itself due to lack of internal support therefor, thus providing minimum restriction and frictional abrasion of the body passageways through which the tube is located. Reintroduction of food in the form of liquid material expands the tube to permit feeding of the patient.

If it is desired to remove liquid material from the stomach of the patient, the support tube 22 may be reinserted into the collapsible tube and passed to the distal end thereof. The support tube 22 of the feeding device can then be employed to suction liquids from the stomach area through distal openings 14, 48 in the respective tubes 11, 22. Withdrawal of the support tube from the collapsible tube is accomplished in the manner previously described.

From the foregoing description of the several embodiments, it can be appreciated that the collapsible tube feeding device of the present invention may be employed for naso-gastric feeding of a medical patient, and may be left in place in the patient's body for extended periods of time with minimum restriction, discomfort and irritation of the body passageways of the patient.

That which is claimed is:

1. A gastric feeding device for introduction into the stomach of a patient from a nasal opening of the patient comprising:

(a) an elongate flexible tube defining a longitudinal passageway therealong, said tube being of a size to permit intubation of same through a nasal opening and the esophagus into the stomach and being adapted to remain intubated for repetitive use, said tube being manufactured of a predetermined material and having a predetermined wall thickness such that said tube collapses along substantially the entire length of same in the absence of internal support, said flexible tube having means adjacent a distal end portion of same to permit passage of feed material from the passageway into the stomach after intubation and to maintain the relative position of a guide-support element receivable along the passageway during intubation;

(b) non-collapsible means associated with a proximal end portion of said flexible tube for introducing a guide-support element and feed materials into said passageway, whereby a guide-support element may be received substantially entirely along said flexible tube during intubation while being held in proper position, after which said guide-support element may be withdrawn, permitting said flexible tube to collapse along its length while intubated to minimize discomfort and other adverse effects to the patient, and whereby introduction of feed materials into said passageway of said flexible tube causes said flexible tube to reopen for passage of said materials, after which said tube again collapses; and (c) a flexible support tube removably received in and extending throughout the length of the passageway of said collapsible tube.

2. A device as defined in claim 1 wherein said means in the distal end portion of said collapsible tube for maintaining the relative position of said elongate support tube therein comprises a wall portion of said collapsible tube at the distal end of said collapsible tube passageway abuttingly engaging the end of said support tube.

3. A device as defined in claim 2 wherein said collapsible tube includes a lateral opening in the wall thereof above the distal end thereof for discharging fluid therefrom into the stomach of a patient.

4. A device as defined in claim 1 wherein said means in the distal end portion of said collapsible tube includes water-soluble adhesive means attached to the interior wall surface of a distal end portion of the collapsible tube and to the exterior wall surface of the distal end portion of the support tube to secure the same together during intubation of a medical patient while permitting release of securement of the collapsible tube and support tube upon contact with water to dissolve the adhesive means.

5. A feeding device as defined in claim 1 wherein said means attached to the proximal end of the collapsible tube comprises a relatively rigid tubular fitting having a passageway therethrough, one end of the passageway connected to the opening in the proximal end of said collapsible tube and the other end of said passageway having an opening for insertion of an elongate flexible support tube into the length of said collapsible tube passageway for internal support thereof, and an opening intermediate the length of the passageway of the tubular fitting for introducing liquid into the collapsible tube throughout its length between the outer wall surface of a support tube therein and the inner wall surface of the collapsible tube.

6. A feeding device as defined in claim 5 wherein means are provided for sealing said other end opening of said tubular fitting and said support tube to seal said other opening against loss of fluid therefrom during and after intubation of a patient.

7. A feeding device as defined in claim 1 wherein said support tube has a longitudinal passageway therethrough and openings at opposite end portions of said support tube for withdrawal of fluid from the stomach of a patient when desired.

8. A feeding device as defined in claim 1 wherein said collapsible tube includes an opening in the distal end of said tube into said tube passageway, and said means for maintaining the position of a support tube in the distal end portion of the collapsible tube passageway includes water-soluble adhesive means closing said distal end opening during intubation of a patient.

9. A method for repetitive introduction of fluent materials into a patient comprising the steps of:

(a) providing an elongate flexible tube, said tube being manufactured of a material that permits collapse of said tube along substantially the entire length of same in the absence of internal support and defines a longitudinal passageway therealong when internally supported, said tube further having means adjacent a distal end of same to permit passage of fluent materials from within said tube when said tube is intubated, said tube further having means associated with a proximal end of same to permit introduction of fluent materials into same;

(b) supporting said tube internally along the length of same to define a longitudinal passageway therealong;

(c) intubating said tube through a nasal opening and the esophagus into the patient's stomach;

(d) removing said internal support while avoiding displacement of said tube whereby said tube collapses along substantially its entire length; and (e) introducing fluent materials into said means at said proximal end of said tube as desired, said fluent materials reopening said passageway adequate for and during material passage therealong whereby said tube remains intubated in a collapsed state when not in use.

* * * * *